United States Patent
Dorsel et al.

(10) Patent No.: US 7,013,220 B2
(45) Date of Patent: Mar. 14, 2006

(54) BIOPOLYMER ARRAY SCANNER WITH REAL-TIME SATURATION DETECTION

(75) Inventors: Andreas N. Dorsel, Menlo Park, CA (US); Jeffrey M. McMillan, Morgan Hill, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 172 days.

(21) Appl. No.: 10/262,124

(22) Filed: Sep. 30, 2002

(65) Prior Publication Data

US 2004/0063105 A1  Apr. 1, 2004

(51) Int. Cl.
  *G01N 33/50* (2006.01)
  *G01N 33/48* (2006.01)
  *G06G 7/00* (2006.01)
  *C12Q 1/68* (2006.01)

(52) U.S. Cl. .............. 702/19; 702/20; 702/22; 702/30; 702/31; 702/32; 702/89; 703/11; 435/6

(58) Field of Classification Search ............ 702/19–29; 435/6; 707/102
See application file for complete search history.

(56) References Cited

U.S. PATENT DOCUMENTS

| 5,091,652 | A | 2/1992 | Mathies et al. |
|---|---|---|---|
| 5,260,578 | A | 11/1993 | Bliton et al. |
| 5,296,700 | A | 3/1994 | Kumagai |
| 5,324,633 | A | 6/1994 | Fodor et al. |
| 5,585,639 | A | 12/1996 | Dorsel et al. |
| 5,760,951 | A | 6/1998 | Dixon et al. |
| 5,763,870 | A | 6/1998 | Sadler et al. |
| 6,078,390 | A | 6/2000 | Bengtsson |
| 6,084,991 | A | 7/2000 | Sampas |
| 6,222,664 | B1 | 4/2001 | Dorsel |
| 6,284,465 | B1 | 9/2001 | Wolber |
| 6,320,196 | B1 | 11/2001 | Dorsel et al. |
| 6,371,370 | B1 | 4/2002 | Sadler et al. |
| 6,406,849 | B1 | 6/2002 | Dorsel et al. |
| 6,471,916 | B1 * | 10/2002 | Noblett ................. 422/82.08 |
| 2003/0160184 | A1 * | 8/2003 | Curry et al. ............. 250/459.1 |
| 2004/0064264 | A1 * | 4/2004 | Corson et al. ................ 702/31 |

OTHER PUBLICATIONS

Agilent G2565AA "Microarray Scnner System with SureScan Technology" UserM anuel, Agilent Technologies, M ay 2002.

* cited by examiner

*Primary Examiner*—Mary K. Zeman

(57) ABSTRACT

Optical scanner system approaches are described in which signal saturation data is produced in real-time. The data generated may be used for tuning a subsequent scan, in protection of optical detector components from damage or otherwise. Approaches for obtaining and storing or expressing the data are also disclosed. Also provided are methods of using the subject system is biopolymer array based application, including genomic and proteomic applications.

13 Claims, 2 Drawing Sheets

BIOPOLYMER ARRAY SCANNER WITH REAL-TIME SATURATION DETECTION

FIELD OF THE INVENTION

This invention relates to biopolymer array optical scanners.

BACKGROUND OF THE INVENTION

Pharmaceutical, biotechnology, or genomics companies use DNA analysis systems for target identification and drug screening in pharmaceutical drug discovery. In many of these systems, biomolecules (e.g., DNA, RNA, cDNA, proteins) labeled with various dyes bind to chips that offer different molecular probe counterparts for binding in different locations of the chip. A scanner is then used to read the fluorescence of these resultant surface bound molecules under illumination with suitable (most often laser) light. The scanner acts like a large field fluorescence microscope in which the fluorescent pattern caused by binding of labeled molecules is scanned on the chip. In particular, a laser induced fluorescence scanner provides for analyzing large numbers of different target molecules of interest, e.g., genes/mutations/alleles, in a biological sample.

The scanning equipment typically used for the evaluation of arrays includes a scanning fluorimeter. A number of different types of such devices are commercially available from different sources, such as Axon Instruments in Union City, Calif. and Perkin Elmer of Wellesly, Mass. Analysis of the data, (i.e., collection, reconstruction of image, comparison and interpretation of data) is performed with associated computer systems and commercially available software, such as GenePix by Axon Instruments, QuantArray by Perkin Elmer or Feature Extraction by Agilent of Palo Alto, Calif.

In such scanning devices, a laser light source generates a—most often collimated—beam. The collimated beam sequentially illuminates small surface regions of known location on an array substrate. The resulting fluorescence signals from the surface regions are collected either confocally (employing the same lens used to focus the laser light onto the array) and/or off-axis (using a separate lens positioned to one side of the lens used to focus the laser onto the array). The collected signals are then transmitted through appropriate spectral filters to an optical detector. A recording device, such as a computer memory, records the detected signals and builds up a raster scan file of intensities as a function of position, or time as it relates to the position. Such intensities, as a function of position, are typically referred to in the art as "pixels" or "pixel values."

If the expected or intended position of the feature is sufficiently close to its true position and laser intensity/detector sensitivity is set appropriately, the pixels within a region centered upon the expected or intended position of a feature can be averaged to yield the relative quantity of target bound to the probe in that feature. However, a user often has little idea of the brightness of the fluorescence that will be emitted by a particular sample. Accordingly, where applicable, the user does not know a priori how high or low to set an attenuator that controls the optical excitation signal power, that is, the signal power that reaches the sample. Likewise, the user will not know how high or low to set the gain of a detector that collects emitted fluorescence and produces a corresponding data signal.

The most apparent value of proper scanner scale factor or sensitivity choice/setup has to do with the amount of reliable information that can be obtained from a scan. Setting laser power and/or detector sensitivity too low may result in failure to collect weak signal information.

Early techniques for adjusting an optical scanner's scale factor involve manually setting the sensitivity of the system, where a user adjusts both the gain of the fluorescence detector and attenuation of the excitation light source. Typically, the user manually scans a sample in raster fashion to locate an element in the micro-array that is known to contain a concentration of a fluorophore that should produce a maximum fluorescence in response to the excitation signal. The user then re-scans the portion of the sample that contains this element and iteratively adjusts the sensitivity of the system until, in the judgment of the user, the corresponding data signal is sufficiently close to a maximum data signal value of the system. If the system has two channels, that is, produces excitation signals using two lasers of different wavelengths, the user re-scans the sample using the signal produced by the second laser/excitation light source and repeats the iterative, manual adjustment process the second channel. A user would further re-scan the sample for each additional channel.

The adjustment ranges for the attenuator or excitation source power and the detector are relatively large. Accordingly, manual adjustment of these components is time consuming. Thus, with manual scanning, the sample may be scanned many times to set the sensitivity of, or calibrate, the system. When multiple channels are used, more time is spent manually calibrating the system and the sample is scanned even more times, as discussed above.

U.S. Pat. No. 6,078,390 to Bengtsson describes a scanning system and method of operation for automatically setting detection sensitivity. It employs an optical scanning system using a low-resolution scanning operation to automatically adjust the sensitivity of the system. The system performs a low-resolution scanning operation by scanning a line, automatically and iteratively setting the levels of excitation signal power and detector gain, skipping a plurality of lines and scanning a next line, adjusting the levels as appropriate, skipping a plurality of lines and scanning a next line, and so forth. After the system sensitivities have been set, the calibrated system then scans all the lines of the sample to actually collect data. The calibrated system thus scans for the first time the lines that were skipped during the low resolution "calibration" scanning operation.

For these skipped lines, photo-bleaching (i.e., weakening of fluorescent signal caused by exposure to excitation light) is avoided. With the other lines, however, the same problems encountered with manual scanning and tuning optical system attenuation or excitation system gain from photo-bleaching as a result of rescanning are encountered. The risk of damage to the sample is further increased when multiple channels are used.

Another approach to setting scanner sensitivity is represented in U.S. patent application Ser. No. 10/910,552, entitled, "Maximum Sensitivity Optical Scanning System," to B. Curry, et al. Here, scans are conducted in an iterative fashion from a maximum sensitivity scan, to scan(s) of lesser sensitivity when saturated results are present. If no signal saturation is detected after completing a scan, one or more increased sensitivity scans may be conducted, to edge system sensitivity upward.

The present invention teaches another approach to setting scanner sensitivity. The approach advantageously offers a less iterative approach in which a quick rescan of features can be made without saturation for improved data acquisition. Further, the invention may be used to safeguard detectors from exposure at too high a signal over too long a period of time. In addition, various data processing options or features may be offered by the present invention.

SUMMARY OF THE INVENTION

The present invention concerns methods related to gathering feature saturation data while scanning an array and the use of such data. Such a system is distinguished from certain known techniques in which saturation data is obtained by post-processing of scan data. Post-processing/data extraction approaches produce a delay—simply by virtue of the calculations that must be run—whereas detecting relevant saturation during a scan allows for shorter "time-to-results" and, thus, higher scanner throughput. The invention is further distinguished from systems that employ iterative scan and adjustment procedures as noted above. Features of the present invention allow for higher scanner throughput by adjusting a scanner upon completion of a first scan to rescan at more optimal settings (without post-processing delays or delay associated with iterative approaches.)

In the present invention, while saturation data compiled during a first scan can be advantageously employed for subsequent scan calibration, it can also (or alternately) be used to protect the detector(s) in the scanner. For instance, saturation levels detected exceeding given parameters can be used to trigger an abort of scanning. In addition to offering approaches for gathering real-time saturation data, and acting upon the same, the present invention teaches certain approaches for handling or storing saturation-related information. Stored data relating to the intensity of saturated features may be used to later interpret the scan data (including the saturated features).

The invention covers such methodology as summarized above and also hardware configured and/or programmed to accomplish the same, each aspect being expressed in further detail below.

DEFINITIONS

Figure 1:
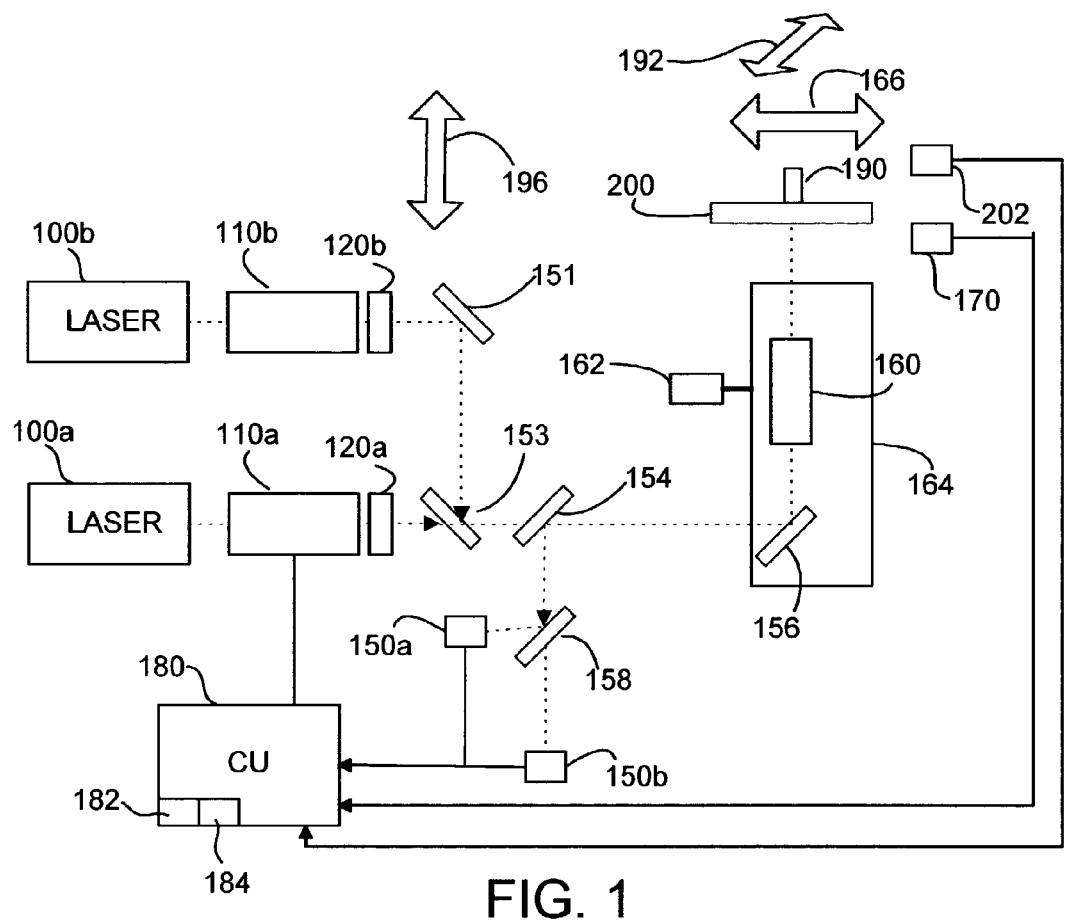
FIG. 1 schematically illustrates an optical scanner as may be used in the present invention.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer/polymer) of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotides with two linking groups one or both of which may have removable protecting groups).

An "array," includes any two-dimensional or substantially two-dimensional (as well as a three-dimensional) arrangement of addressable regions bearing a particular chemical moiety or moieties (e.g., biopolymers such as polynucleotide sequences (nucleic acids), polypeptides (e.g., proteins), etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 $\mu m$ to 1.0 cm. In other embodiments each feature may have a width in the range of 1.0 $\mu m$ to 1.0 mm, usually 5.0 $\mu m$ to 500 $\mu m$, and more usually 10 $\mu m$ to 200 $\mu m$. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm², or even less than 50 cm², 10 cm² or 1 cm². In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. Nos. 5,599,695, 5,753,788, and 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top, upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

By "saturation" it is meant the condition of a scanner channel topping-out or getting pegged at the upper end of its range (e.g., 65535 for a $2^{16}-1$ bit range) by a high signal. By "background" or "background signal" it is meant the scan signal that arises from scanning a substrate in an area with no signal-producing material present.

DETAILED DESCRIPTION OF THE INVENTION

In describing the invention in greater detail than provided in the Summary and as informed by the Background and Definitions provided above, the subject program or process aspects of the invention are first described. Next, an exemplary optical scanner is described, including invention-specific hardware aspects of the same. This discussion is followed by a description of methods of using scanners in accordance with the present invention, kits for use in the invention and an exemplary implementation.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Methodology/Programming

As summarized above, the present invention involves software control for a scanner or optical imaging system, preferably a biopolymer array optical scanner, and associated methodology for detecting and/or acting upon pixel saturation information. Generally, real-time saturation data is produced. That is to say, saturation data is produced during scanning.

Programming embodying the methodology may be loaded onto an optical scanner, or the scanner may be preprogrammed to run with the same. The scanner used is preferably one suited for scanning biopolymer arrays. Any number of scanners will be suitable for such purposes, especially those noted herein.

In any case, the saturation data generated during scanning may be utilized in a variety of ways. These methods include taking prophylactic measures to protect the scanner, adjusting settings for a subsequent scan and/or processing scan data. Memory features for storing saturation data generated during scanning possibly in connection with non-saturated scan results—may be employed or may be used to facilitate any such action.

In a first aspect of the invention, data correlated to saturation is generated when detection circuitry employed in a scanner (i.e., electrometer(s) and/or A/D converter(s)) lock to or produce a zero output for a short time after a sufficiently strong saturated feature is encountered. On the far side of a scanned feature (considering the scan direction) that is saturated, signal drops-off from the "background" signal due to the locking is then observed. Thus, a pixel preceding a "dim" pixel is, in fact, saturated.

For scan results of a given feature scanned only in one direction, the background level presented adjacent strongly saturated features should actually be about zero (not accounting for measurement errors). However, where scan results are produced by binning together scan results for the same data or adjacent rows of data scanned in opposite directions, data pixels showing zero background levels are combined, and thus averaged, with pixels showing full background levels. This action still results in the background level presenting at a value above zero, but lower than typical—theoretically—50% of "background" signal. For further discussion of pixel binning approaches, see U.S. patent application Ser. No. 10/210,848, filed Jul. 31, 2002 entitled, "Array Scanner Noise Reduction System."

Hence, detecting pixels presenting at lower than expected background provides a means of detecting saturation (particularly, strong saturation) during scanning. To hedge against random and systematic measurement errors some value between the background signal level and the 50% background signal mark will allow for detecting saturated features with either type of scan approach noted above. Splitting the difference, one may choose to count saturated features as those presenting at 75% of background signal level. Still, more sophisticated approaches may utilized in determining what threshold values is used in detecting or checking for saturated features by this methodology.

Saturated features may be detected in other manners as well. For example, a detection circuit (not shown) may be provided in connection with the optical detector(s) included in the optical scanner, the circuit being configured to set a flag or keep count of where a signal of a given intensity is reached. This threshold value may involve current levels in connection with the detection device, voltage levels with any included electrometer, or the pixel intensity value (especially a pixel value at or near the available data range provided for measuring pixel intensity) with any ADC(s).

In addition to simply detecting or checking for saturated features, supplemental detector hardware—examples of which are described in FIGS. 2B and 2C below—may be capable of producing a measure of the intensity of the saturated result over a first detector circuit. However such action is accomplished, the measure of the saturated feature intensity may be correlated to how many fold or times over-bright the feature is relative to the saturation level of the first detector circuit or subsystem which is set to a higher sensitivity in order to gather data from dimmer features.

However generated or presented, such a metric of a "saturation factor" (i.e., how many times too-bright a feature is relative to a given reference) may be applied to alter excitation light source intensity and/or PMT/detector device gain or attenuation for a subsequent scan. In which case, the subsequent scan is made at or nearly at optimal settings. Rescanning in this manner should produce no or very few saturated results (or resultant locking) while achieving the highest signal level compatible with this condition. In addition, it should eliminate striping issues otherwise observed. Particularly, it will avoid the situation when adjacent lines that are scanned in alternate directions show a stripe pattern next to a saturated feature (as opposed to striping resulting from bleaching of previous scans.

In adjusting the scanner, it may be preferred to utilize a maximum PMT gain/sensitivity and lower excitation light source levels to avoid photobleaching to the extent possible, in case further scans may be conducted (e.g., for additional scanner channels). However the scanner is adjusted though, a speedy, non-iterative approach to scanner tuning is enabled by use of the information gathered in real-time regarding relative intensity of saturated features.

Real-time saturation data produced according to the present invention may be employed to initiate rescanning a number of ways. In one approach, data indicative of an overall saturated pixel count reaching a threshold level may trigger rescanning. Alternately (or additionally), rescanning may be prompted if one or more saturated features are too bright, e.g., saturated by about 1.1, about 1.5 and about 3 fold or more, where these stated values provide a useful threshold value and more robust higher trigger values, respectively.

The saturation factor used to adjust scanner setting may be generated in reference to the brightest pixel in a scan, or a statistically relevant number of pixels at a given level. Alternately (or additionally) a scale factor may be produced for all saturated pixels of a scan (possibly up to a maximum count and/or level).

In the event a saturation scale factor is generated for each saturated pixel, it may be applied to the high sensitivity scan results (which include the saturated features) in order to construct a wide dynamic range output. The saturation factors can be used as multiplers for the intensity of their respective saturated pixel values to construct such an output of scan results.

Still, it is contemplated that when the real-time saturation data triggers a rescan, that such data is not also used for setting scanner scale factor(s). A simplified system could simply direct rescanning at a preselected lower setting (e.g. some particular predetermined settings), or at settings lowered by some preselected lower ratio (e.g., dropping setting/ scanner sensitivity by a factor of 2, 3, 4, etc. relative to the settings at which the saturated results were produced). Actually, in this instance where a full set of real-time saturation data is not required to adjust the scanner (because the presence of saturated data is merely used as a rescan trigger), scanner throughput may be increased by terminating a scan part-way and beginning again at lower settings.

Another use for saturation data concerns protecting scanner detectors (such as any included PMT) that are sensitive to or can be damaged by overexposure to light. In the event that an overly large percentage of results are saturated, controller 180 or a dedicated protection switch (not shown) can be configured (directly or via software control) to abort scanning. Similarly, where data representative of the degree of saturation is generated, abortion of scanning can be ordered in view of the relative brightness of saturated results. Still further, scanning may be prematurely terminated in the event of some combination of saturation frequency and intensity of features.

Real-time saturation-related data is preferably stored in some manner, possibly for use as described above in scanner tuning or data generation, though other uses may be presented. The stored saturation data may take the form of a numerical code corresponding to saturation pixel count/ frequency and/or its relative intensity. The data may be used to avoid feature extraction of scan data (by which scan results are post-processed to obtain a count for saturated pixels), since such information is inherent to either sort of data produced according to the present invention.

Programming according to the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information.

Optical Scanners

Also provided by the subject invention are biopolymer array optical scanners that are programmed as described above. Any biopolymer optical scanner or device may be provided to include the above programming. Representative optical scanners of interest include those described in U.S. Pat. Nos. 5,585,639; 5,760,951; 5,763,870; 6,084,991; 6,222,664; 6,284,465; 6,329,196; 6,371,370 and 6,406,849—the disclosures of which are herein incorporated by reference. An exemplary optical scanner as may be used in the present invention is shown in FIG. 1.

A light system provides sample excitation light from a source such as a laser 100. The light passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light beam exiting from the attenuator.

The light from both lasers 100a, 100b is transmitted through a dichroic beam splitter 154, reflected off fully reflecting mirror 156 and focused onto either an array (not shown) mounted on holder 200, or a calibration member (not shown), whichever is at a reading position, using optical components in beam focuser 160. Light emitted (in particular, fluorescence) at two different wavelengths (e.g., green and red light) from features 16, in response to the interrogating light, is imaged using the same optics in focuser/ scanner 160, and is reflected off mirrors 156 and 154. The two different wavelengths are separated by a further dichroic mirror 158 and are passed to respective detectors 150a and 150b.

More optical components (not shown) may be used between the dichroic and each detector 150a, 150b; splitter 154 or mirror 158 (such as lenses, pinholes, filters, fibers, etc.) and each detector 150a, 150b may be of various different types (e.g., a photo-multiplier tube (PMT) or a CCD or an avalanche photodiode (APD)). All of the optical components through which light emitted from an array or calibration member in response to the illuminating laser light, passes to detectors 150a, 150b, together with those detectors, form a detection system. A scan system causes the illuminating region in the form of a light spot from each laser 100a, 100b, and a detecting region of each detector 150a, 150b (which detecting region will form a pixel in the detected image), to be scanned across multiple regions of an array or an array package mounted on holder 200.

Figure 2A:
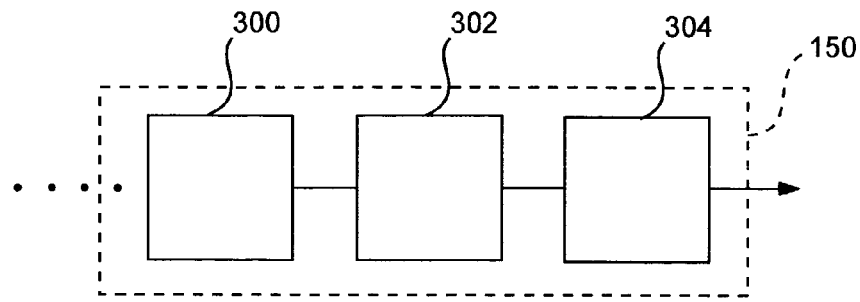
FIGS. 2A–2C schematically illustrate various detector hardware as may be used in the present invention.
Figure 2B:
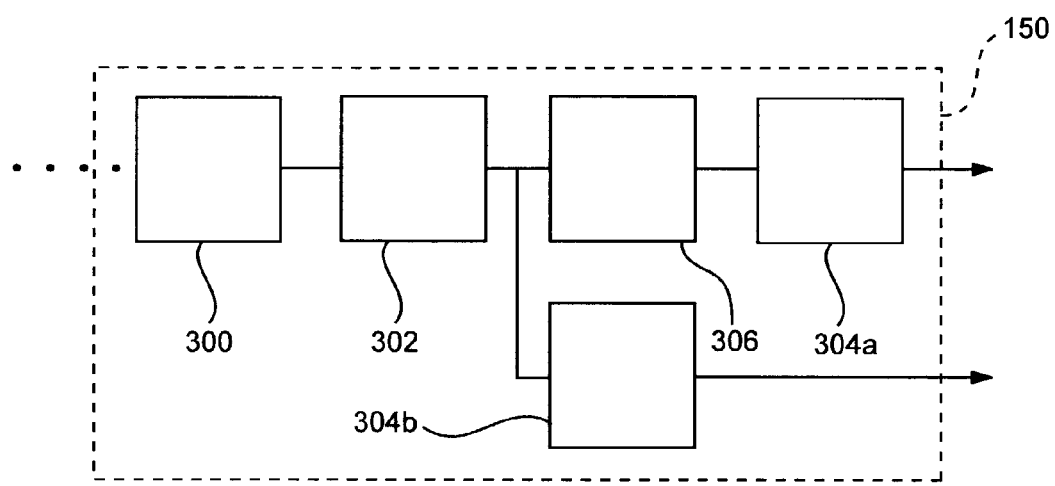
Figure 2C:
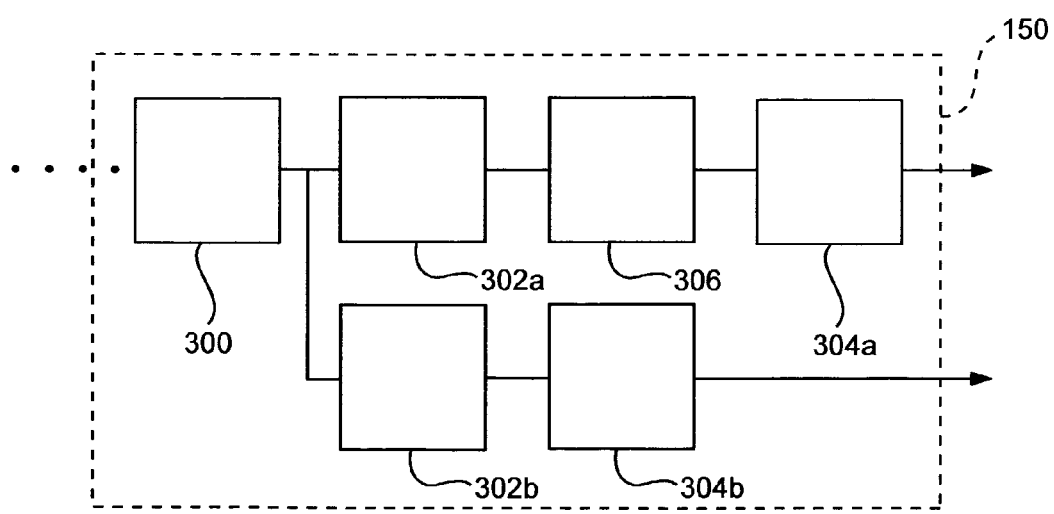

Each detector 150 may be configured as shown in any of FIGS. 2A–2C, with such ancillary components as required. In FIG. 2A, a PMT, CDD, APD or other light detecting device 300 is provided. Ideally, such a device generates current proportional to the intensity of light in its detection region. To convert the proportional current to proportional voltage, an electrometer 302 is operatively coupled to element 300. The voltage-based signal is then provided to an Analog-to-Digital converter (ADC) 304 providing a digital output corresponding to signal intensity.

In FIG. 2B a detector subsystem 150 as may be employed in certain methodology described above is shown. First and second ADCs, 304a and 304b, follow a light detecting device 300 and an electrometer 302. A signal limiter (such as a voltage limiter) 306 may be provided before either ADC, but is preferably provided to protect ADC 304a which is set to a higher sensitivity than ADC 304b in use. FIG. 2C shows another configuration that may be preferred in practicing methods according to the present invention. In this detector variation, electrometer/ADC combinations are decoupled. Particularly, a first electrometer 304a is operatively connected to a first ADC 304a (also, an intermediate voltage limiter 306 may be provided as above); a second electrometer 304b is operatively connected to a second ADC 304b. Such decoupling may decrease any undesirable effect the limiter might otherwise have on the input signal of the other ADC.

As provided, the detectors in FIGS. 2B and 2C are suitable for producing real-time or on-the-fly feature saturation data. Whereas the incoming signal for the first ADC 304a in each subsystem may exceed its resolution (i.e., register as a saturated result) the second ADCs 304b are set to accept a higher input voltage. Accordingly, they are able to register a non-saturated result.

The pixel intensity value obtained from the second ADC 304b in each of the detectors 150 in FIGS. 2B and 2C can preferably be related to the maximum or saturated level of the fist ADC 304a in each subsystem. One way in which this may be accomplished is simply by considering the relative setting of each. In the detector system of FIG. 2C, where separate electrometers are provided, differences between their setting should be considered as well. The relative input/output characteristics of such devices may be appreciated by routine testing to generate calibration/scale factor data or by such information provided by the component vendors. Such data could be stored in the scanner for automatic application to measurements or to automatically be added to output data files generated. The second electrometer 302b can also be designed to be highly non-linear to provide for expression of a large signal range (e.g., by providing the log of the input signal).

However the detector(s) 150 are configured, the scanned regions for an array will include at least its multiple probe features. The scanning system is typically a line by line scanner, scanning the interrogating light in a line across an array as described below when at the reading position, in a direction of arrow(s) 166, then moving ("transitioning") the interrogating light in a direction into/out of the paper as depicted by arrow(s) 192 as viewed in FIG. 1 to a position at an end of a next line, and repeating the line scanning and transitioning until the entire array has been scanned.

This scanning feature is accomplished by providing a housing 164 containing mirror 156 and focuser 160, which housing 164 can be moved along a line of pixels (i.e., from left to right or the reverse as viewed in FIG. 1) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 1 may further include a reader (not shown) to read an identifier from an array package. Such an identifier may be in the form of a bar code that can be read by a suitable bar code reader.

Of course, the movements 166 and 192 may be accomplished by actuating holder 200 or housing 164 alone. Still further, the movement roles described for each element above may be swapped.

An autofocus detector 170 is generally provided to sense any offset (variation in slope) between different regions of array 12 when in the reading position, and a determined position of the focal plane of the detection system. The autofocus system includes detector 170, processor 180, and a motorized or servo-controlled adjuster 190 to move holder 200 in the direction of arrow 196 to establish correct focus for the system. The detector may directly detect a partial reflection from another beamsplitter (not shown) (e.g., between splitters 153 and 154). In addition, a second position detector 202, also feeding back to the CU, preferably measures the absolute position (i.e., relative to the apparatus) of the servo-controlled adjuster 190. As above with respect to movements 166 and 192, it should be observed that focus servo control movement indicated by arrows(s) 196 may occur in connection with housing 164 or focusing optics 160 instead of the holder. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors—the disclosures of which are herein incorporated by reference. In addition, details regarding maintaining or setting lens focus upon changing direction may be appreciated in reference to U.S. patent application Ser. No. 10/087,220, entitled "Bi-Directional Scanner Control System," filed Feb. 28, 2001 which provides algorithms to account for variability in assay slide slope—the disclosure of which is herein incorporated by reference.

In any case, array orientation and configuration is of little consequence in this context (though it may be in other situations) since focus can be set to probe features either directly, or looking through a transparent substrate medium if the array is inverted for scanning.

Controller 180 of the apparatus is connected to receive signals from detectors 150*a*, 150*b*, these different signals corresponding to different "channels," i.e., signals which result at each of the multiple detected wavelengths from emitted light for each scanned region of an array when at the reading position mounted in holder 200. Controller 180 also receives the signal from autofocus offset detector 170 and absolute servo position detector 202, and provides the control signal to EOM 110, and controls the scan system. Controller 180 may also analyze, store, and/or output data relating to emitted signals received from detectors 150*a*, 150*b* in a known manner.

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network, possibly a wireless network) with a remote site (such as a database at which information relating to array package 30 may be stored in association with the identification 40).

The controller is suitably programmed to execute all of the steps required by it during operation of the apparatus. Alternatively, controller 180 may be any hardware or hardware/software combination which can execute those steps.

Utility

The subject biopolymer optical scanners find use in a variety applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as an isotropic or radioactive or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids (or other molecules) that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143,854; 5,288,644; 5,324, 633; 5,432,049; 5,470,710; 5,492,806; 5,503,980; 5,510, 270; 5,525,464; 5,547,839; 5,580,732; 5,661,028; 5,800, 992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436, 170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

Figure 3:
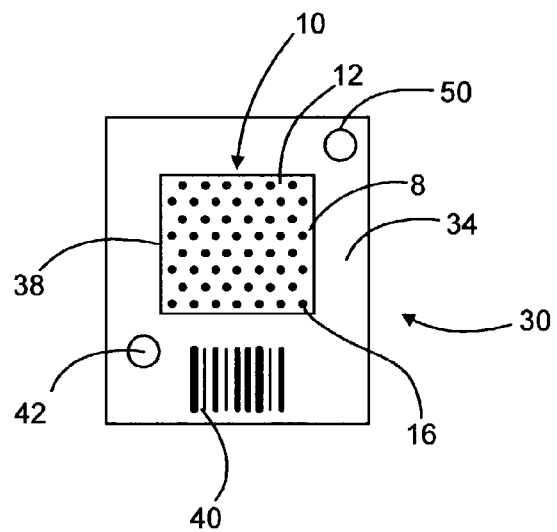
FIG. 3 is a front view of a packaged array that may be used in connection with scanners according to the present invention.

An exemplary array is presented in FIG. 3. Array 10 carries multiple probe features 16 disposed across a surface of the substrate 12. The substrate is preferably in the form of a contiguous, substantially planar substrate made of transparent material to facilitate data acquisition scanning there through. Alternatively, the substrate could be scanned from the side which carries features 16. Features 16 (not to scale) are shown disposed in a pattern which defines the array. The extent of the pattern defines a scan region 8. (Difference between 8 and 10 not clear from drawing.)

Array 10 may be set within a housing 34 to provide an array package 30. In which case, substrate 10 is sealed (such as by the use of a suitable adhesive) to housing 34 around a margin 38. Housing 34 is configured such that housing 34 and substrate 12, define a chamber into which features 16 of the array face. This chamber is accessible through resilient septa 42, 50 which define normally closed ports of the chamber. An identifier 40, possibly in the form of a bar code, may be affixed to housing 34. The composition of the probe features and material(s) used to produce elements of the array package may vary, but may be as typical in the art.

In using an array in connection with a programmed scanner according to the present invention, the array will typically be exposed to a sample (such as a fluorescently labeled analyte, e.g., protein containing sample) and the array will then be read. Reading of the array may be accomplished by illuminating the array and reading the location and intensity of resulting fluorescence at each feature of the array to detect any binding complexes on the surface of the array. It is further noted that aspects of the invention may be applicable to a variety of optical scanners including those that detect chemiluminescent or electroluminescent labels.

In any case, results from reading an array may be raw results (such as fluorescence intensity readings for each feature in one or more color channels) or may be processed results such as obtained by applying saturation factors to the readings, rejecting a reading for a feature which is above or below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, Internet, etc.

Kits

Kits for use in connection with the subject invention may also be provided. Such kits preferably include at least a computer readable medium including instructions and programming embodying or adapted to direct the functionality as discussed above. The instructions may include software installation or setup directions to program an otherwise ordinary scanner so to function as described. The instructions may include directions for directing the scanner to perform as desired. Preferably, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Of course, some form of access security or identification protocol may be used to limit access to those entitled to use the subject invention. As with the instructions, the means for obtaining the instructions and/or programming is generally recorded on a suitable recording medium.

The following examples are offered by way of illustration and not by way of limitation.

EXAMPLE

In connection with an Agilent model G2565AA or G2565BA scanner running software according to the present invention, an "image file" it outputs may be employed to store saturation data. For example, one can take the "n" highest numbers representing pixel intensity data and reserve them to store saturation information. In such an approach, where pixel results are expressed in terms of $2^{16}-1$ or 16 bits, a saturated pixel may be represented by a value of up to 65535 (corresponding to a value 10-fold over saturation level), 65534 (corresponding to a value 9-fold over saturation level), . . . 65527 (corresponding to a value 2-fold over saturation level), etc. In the instance noted above where saturation is detected in connection with adjacent dimmer pixels, these pixels may be used to store saturation data using the lowest "n" numbers. Stored thus, it takes a reduction of the data range by less that 1% to store saturation factors up to 5-fold with an error of 1% or less. Larger portions or higher percentages of the data range, for example, upwards of about 5%, but typically less than 10% may also be employed.

Either sort of data storage allows for display of scan results using typical software in a more-or-less conventional manner. However, with dedicated software (such as product G2566AA by Agilent offered with its scanners), a user can employ the additional stored data stored to produce nearly backwards-compatible large-dynamic range results. Alternately, the stored information can be used in connection with methodology discussed above or otherwise. Furthermore, while the information may be stored in a linear data format (such as expressed above) an abscissa/exponent may alternately be employed.

Though the invention has been described in reference to certain examples, optionally incorporating various features, the invention is not to be limited to that specifically described. It is to be understood that the breadth of the present invention is to be limited only by the literal or equitable scope of the following claims.

It is evident from the above discussion that the above described invention provides an effective and readily applicable way to extend the lifetime of optical scanners. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of scanning a biopolymer array with an optical scanner, said method comprising:
   scanning a plurality of array features to obtain scan results, and
   checking for saturated pixels in real-time during said scanning.

2. The method of claim 1, further comprising:
   terminating scanning in response to detecting at least one pixel below a background signal level.

3. The method of claim 1, wherein said checking for saturated pixels is accomplished by checking for pixels with an intensity below a background signal level.

4. The method of claim 3, wherein said checking is for pixels with an intensity below about 75% of said background signal level.

5. The method of claim 1, further comprising:
   measuring an intensity of a saturated pixel preceding a pixel of intensity below a background signal level.

6. The method of claim 5, wherein first and second detection circuits are provided, said first circuit being locked to a zero output by said preceding pixel intensity, said second circuit providing an intensity result for said preceding pixel.

7. The method of claim 5, wherein said second circuit result provides a saturation factor in preparing scanner results.

8. The method of claim 7, wherein said second circuit result is utilized in scanner adjustment for a subsequent scan of said array.

9. The method of claim 1, wherein said biopolymer array is chosen from a polypeptide array and a nucleic acid array.

10. The method of claim 1, wherein said checking for saturated pixels during scanning comprises evaluating a signal from one or more previously scanned pixels.

11. The method of claim 1, wherein said checking for saturated pixels is by checking for a pixel of an intensity about at the maximum of a pixel data range.

12. An optical scanner system programmed to operate according to a method chosen from the methods of claims 1–11.

13. A computer-readable medium comprising a program to direct an optical scanner system to perform a method chosen from the methods of claims 1–11.

* * * * *